United States Patent [19]

Ruckdeschel et al.

[11] Patent Number: 5,251,801
[45] Date of Patent: Oct. 12, 1993

[54] SURGICAL STAPLER

[75] Inventors: Thomas W. Ruckdeschel, Apex; John C. Phillips, Holly Springs, both of N.C.

[73] Assignee: Edward Weck Incorporated, Princeton, N.J.

[21] Appl. No.: 924,172

[22] Filed: Aug. 3, 1992

Related U.S. Application Data

[63] Continuation of Ser. No. 740,505, Aug. 5, 1991, Pat. No. 5,170,926.

[51] Int. Cl.⁵ .......................................... A61B 17/068
[52] U.S. Cl. ..................................... 227/177; 227/19; 227/120
[58] Field of Search .................. 227/175, 176, 177, 19, 227/109, 120, 125, 126

[56] References Cited

U.S. PATENT DOCUMENTS

| | | | |
|---|---|---|---|
| 4,478,362 | 10/1984 | Foslien | 227/120 X |
| 4,591,086 | 5/1986 | Campbell et al. | 227/120 X |
| 4,796,793 | 1/1989 | Smith et al. | 227/19 |
| 4,951,860 | 8/1990 | Peters et al. | 227/177 |

Primary Examiner—Frank T. Yost
Assistant Examiner—Rinaldi Rada
Attorney, Agent, or Firm—Rosenblatt & Associates

[57] ABSTRACT

A hand-held surgical stapler is provided having a reduced distal profile due to a unique feeding means. A combination of features allows the reduced distal profile. The staple storage cover can be of reduced distal thickness due to the slope effect. The staple pusher has the capability at its distal end to push and by pushing lift all of the staples, including the last, into the staple track. Provisions are made on the staple pusher to allow the form tool to displace it out of the staple track to allow forming of the last staple. Nose assemblies are disclosed which can be interchangeably mounted to various trigger assemblies. The pre-load on the stored staples can be varied. A ratchet feature requires full depression of the trigger before it can be returned to a neutral or extended position and full extension of the trigger to its neutral position prior to initiation of the next staple feed cycle.

4 Claims, 10 Drawing Sheets

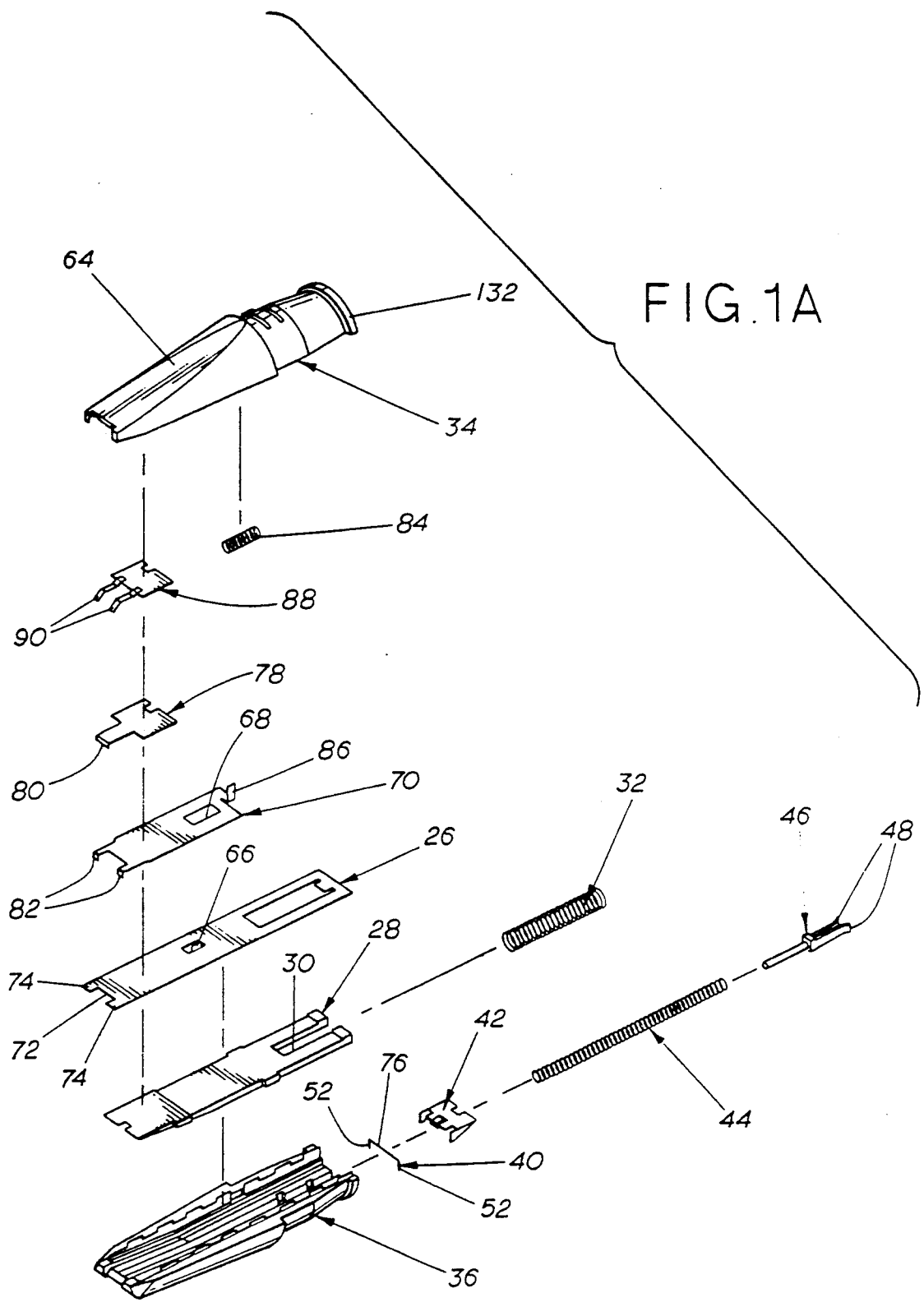

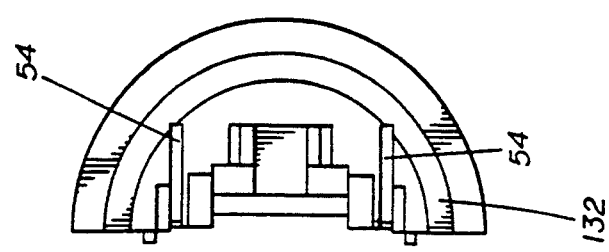
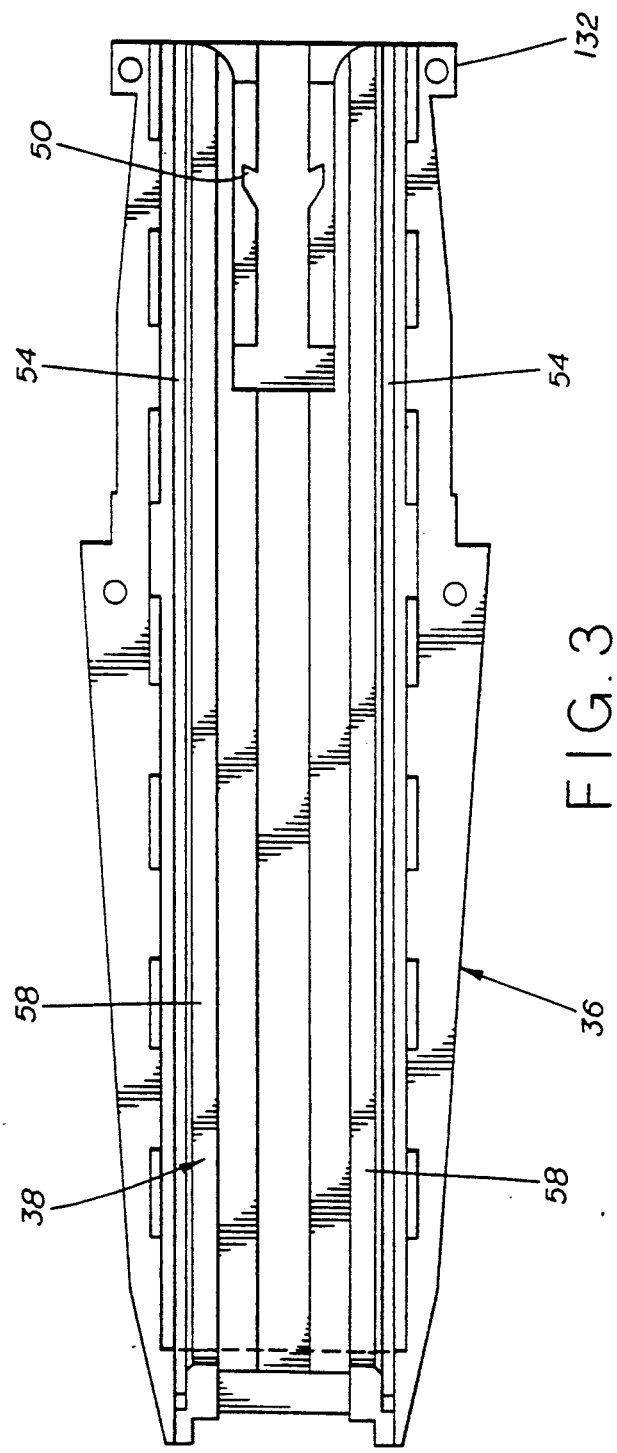
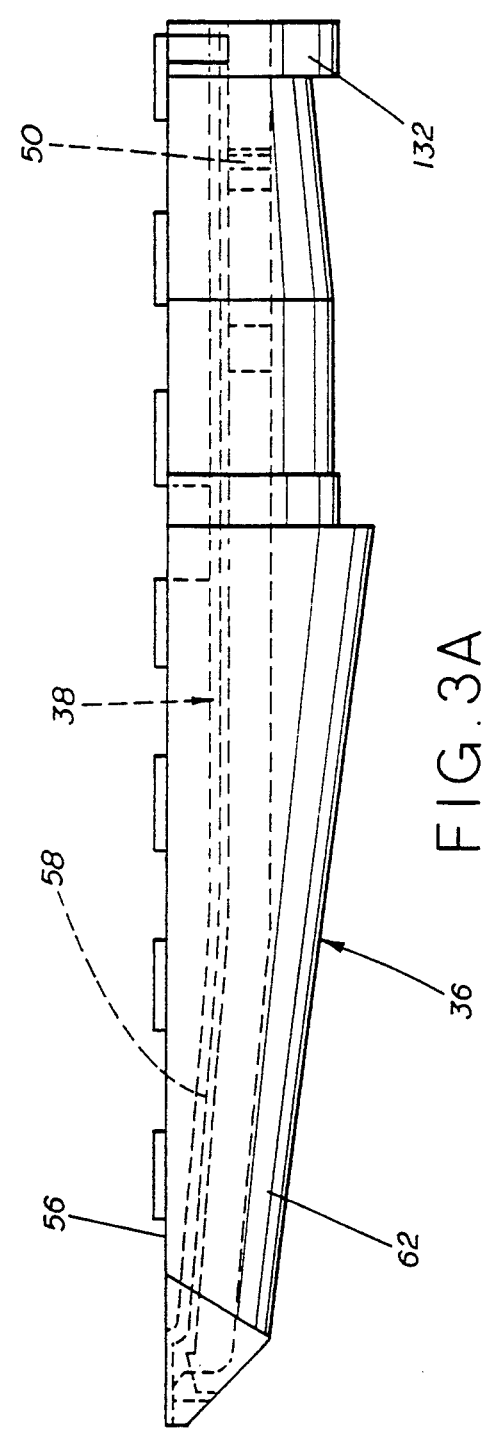

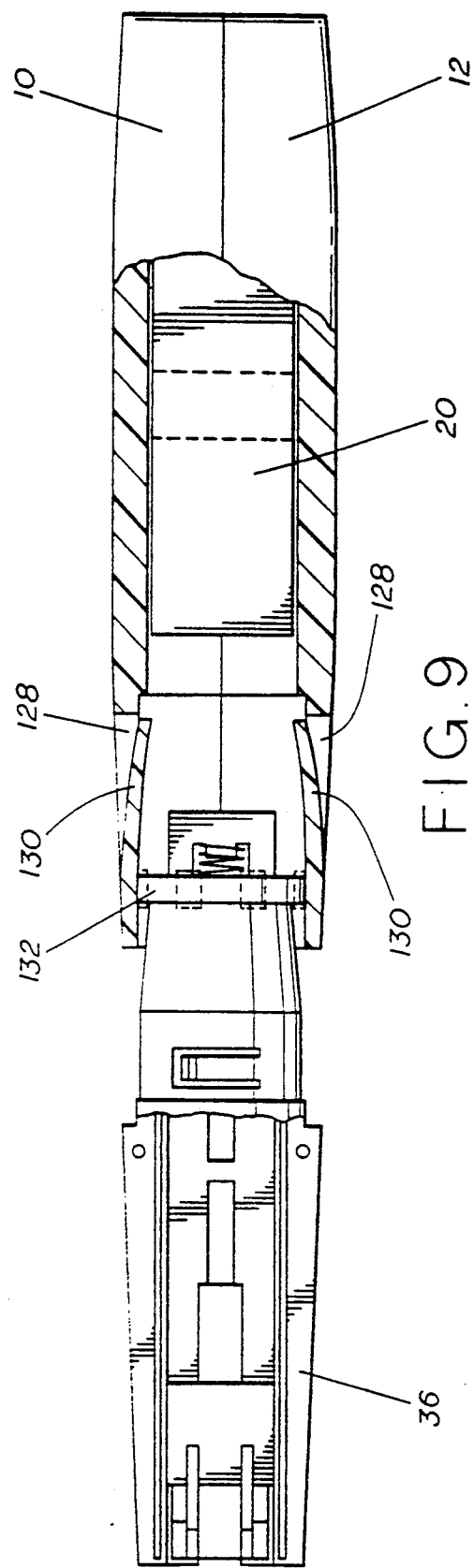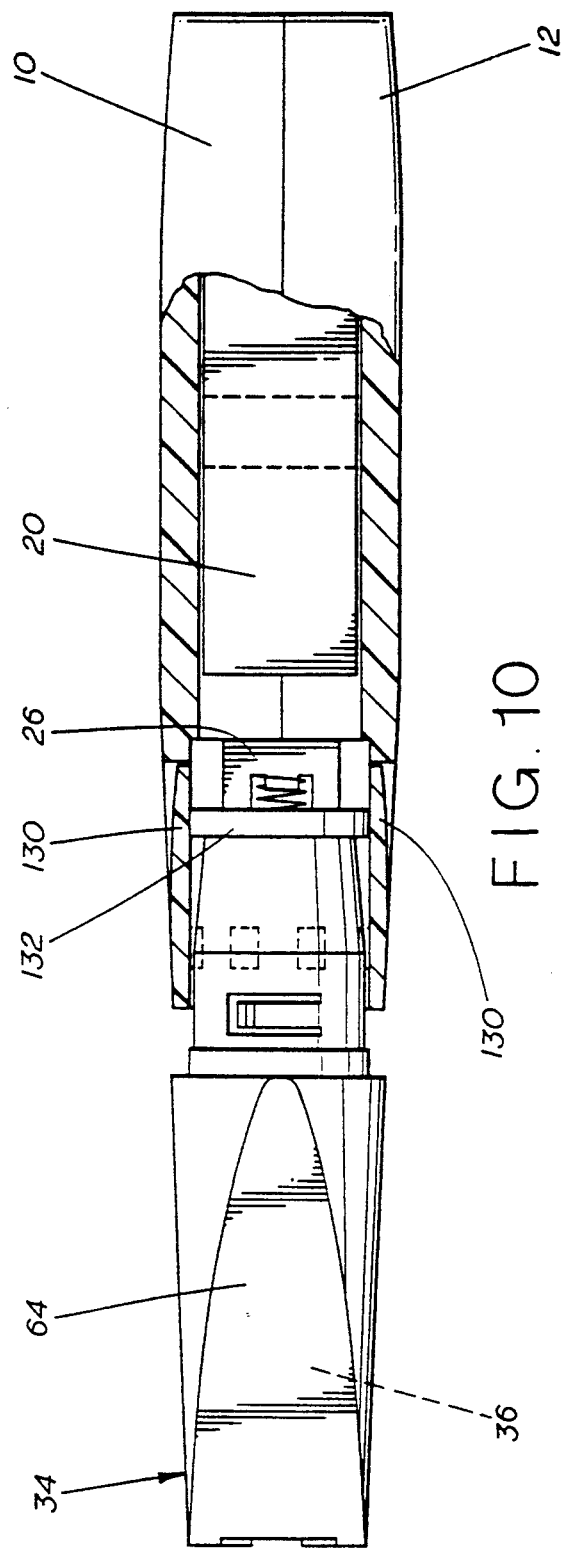

SURGICAL STAPLER

This is a continuation of copending application Ser. No. 07/740,505 filed on Aug. 5, 1991 now U.S. Pat. No. 5,170,926.

FIELD OF THE INVENTION

The field of this invention relates to hand-held surgical staplers.

BACKGROUND OF THE INVENTION

Hand-held surgical staplers have been in use for some time. These staplers feature a magazine to store staples prior to dispensing, a mechanism to feed staples, and another mechanism to form them as they are discharged from the apparatus.

From an ergonomic point of view, the hand-held stapler needs to have a low distal profile to allow the surgeon maximum visibility of the closure site as the staples are formed to close in incision. Another important criteria for surgical staplers is the ability to reliably feed staples as needed without clogging or jamming. The need to reliably feed staples exists concerning the first staple to be fed in a series all the way down to the last remaining staple in the magazine.

Another desirable feature would be an interchangeable feature allowing different nose assemblies to be used with a trigger assembly to facilitate continuing use of the apparatus during a closure procedure. The interchangeable feature also allows flexibility in production since a nose assembly would be usable with a variety of handle assemblies. This advantageous feature is incorporated in the apparatus of the present invention. Also, a feature of the apparatus of this invention is a layout of the staple track permitting a narrow or distal profile promoting visibility of the incision. The staple delivery method has been improved to reliably feed staples down to the last staple in the track so that the apparatus functions reliably.

The apparatus of the present invention is configured to allow maximum wound site access and staple visibility during placement and formation of the staple. The apparatus has a capacity for storage of a large number of staples which is a practical convenience for the surgeon. Due to the overall simple design of the stapler of the present invention, it can be economically built for reliable operation. Compactness of the rotating head stapler of the present invention, especially at the distal end, is a significant attribute.

The apparatus contains a high capacity staple track. The staples are stacked against each other on end to allow storage of as many staples as possible in a compact space. Some prior art designs stored the staples laying on their sides flat, as on a table, one behind the other. When stored in such manner, the capacity of a stapler is significantly reduced. To ensure compactness in the apparatus of the present invention, the staple track is oriented back along a plane roughly parallel to the form tool plane. To form the staples, they must be oriented into the firing position where the form tool can move them against the anvil for staple formation.

To this end, the apparatus of the present invention involves a unique manner of reorienting the staples into the firing position. To do this, the staples must be moved around a curved portion at the distal end of the staple track and through an opening into the path of the form tool. To accomplish this in the prior art, the staple pusher has been made flexible so that the last few staples can be pushed around the curved portion of the staple track. The staple pusher has to be flexible enough to move in the curved portion of the track. While use of a smaller radius at the distal portion of the staple track reduces the distal profile of the stapler, it creates more difficulties in producing a staple pusher flexible enough to traverse the smaller radius curves without excessive friction.

The approach in the prior art has been to utilize a relatively large radius at the distal end of the staple track and to orient the staple track in an angled manner of approximately 15° from the form tool plane. This resulted in a very bulky rotating distal portion. Another problem with the use of fairly small radiuses at the distal end of the staple track is that the staples in the track are pre-loaded toward the distal end of the track. One way to accomplish the pre-load is to locate a compression spring at the proximal end of the staple stack. It then follows that the pre-load will be at its lowest for the last few staples in the stack. If this decrease in pre-load for the last staples is coupled with the need to advance those last staples around a fairly small radius bend, a significant design constraint is presented for staplers of the prior art. The stapler of the present invention has solved this problem by virtue of its features disclosed with regard to the sloping of the staple track with respect to the form tool path. The sloping of the staple track allows the staple cover to be thinner at its distal end. This reduces the height that the staples must be picked up at the distal end of the staple track to get them into the form tool path. It is this feature, coupled with the staple pusher incorporating a "fin" design, that allows the apparatus of the present invention to reliably feed all of the staples in the track into the form tool path. The fin is uniquely shaped to reliably feed up to the last staple and the staple pusher is configured so that the fin is deflected out of the form tool path by the advancing form tool.

By providing these features, the stapler of the present invention overcomes the design limits of prior designs in solving the problem of being able to reliably feed staples up to the last staple in a feed path involving a small radius bend at the distal end of the staple track.

Prior designs of surgical hand-held staplers are illustrated in U.S. Pat. Nos. 4,951,860; 4,662,555; and 4,807,628. These patents show staples stored on a track being fed into a feedpath and finally pushed against an anvil where they are formed and ejected from the stapler.

FIGS. 3 and 4 of U.S. Pat. No. 4,662,555 illustrate a feature which requires completed motion of the trigger handle in either direction before it can be reversed. With this feature, the trigger must be depressed completely before it is allowed to be returned to its neutral position. This allows the surgeon some flexibility while the staple is not fully formed to position the gun prior to full closure of the staple. The requirement that the trigger must come all of the way out before the next cycle can begin prevents misfeeding of staples into the staple track.

Other hand-held surgical staplers having one or more of these features can be seen in U.S. Pat. Nos. 4,391,402; 4,196,836; 4,592,498; 4,523,695; 4,598,711; 4,049,177 (tag attaching apparatus); and European Patent Application 0040157.

Also, of general interest in the attachment art, are U.S. Pat. Nos. 4,077,557 (illustrating a tool used in producing printed circuit assemblies); 4,125,215 (showing a tag attachment apparatus); and 2,228,778 (illustrating a desktop stapler).

SUMMARY OF THE INVENTION

A hand-held surgical stapler is provided having a reduced distal profile due to a unique feeding means. A combination of features allows the reduced distal profile. The staple storage cover can be of reduced distal thickness due to the slope effect. The staple pusher has the capability at its distal end to push and and by pushing lift all of the staples, including the last, into the staple track. Provisions are made on the staple pusher to allow the form tool to displace it out of the staple track to allow forming of the last staple. Nose assemblies are disclosed which can be interchangeably mounted to various trigger assemblies. The pre-load on the stored staples can be varied. A ratchet feature requires full depression of the trigger before it can be returned to a neutral or extended position and full extension of the trigger to its neutral position prior to initiation of the next staple feed cycle.

DETAILED DESCRIPTION OF THE DRAWINGS

FIGS. 1 and 1A are exploded views of the apparatus of the present invention.

FIGS. 3 and 3(A-B) are side, top, and end views of the staple track.

FIGS. 9 through 11 illustrate the snap fit between the nose assembly and the trigger assembly.

DETAILED DESCRIPTION OF THE PREFERRED EMBODIMENT

The disclosures in U.S. Pat. Nos. 4,951,860; 4,807,628; and 4,662,555 are incorporated in this application in full.

Figure 1:
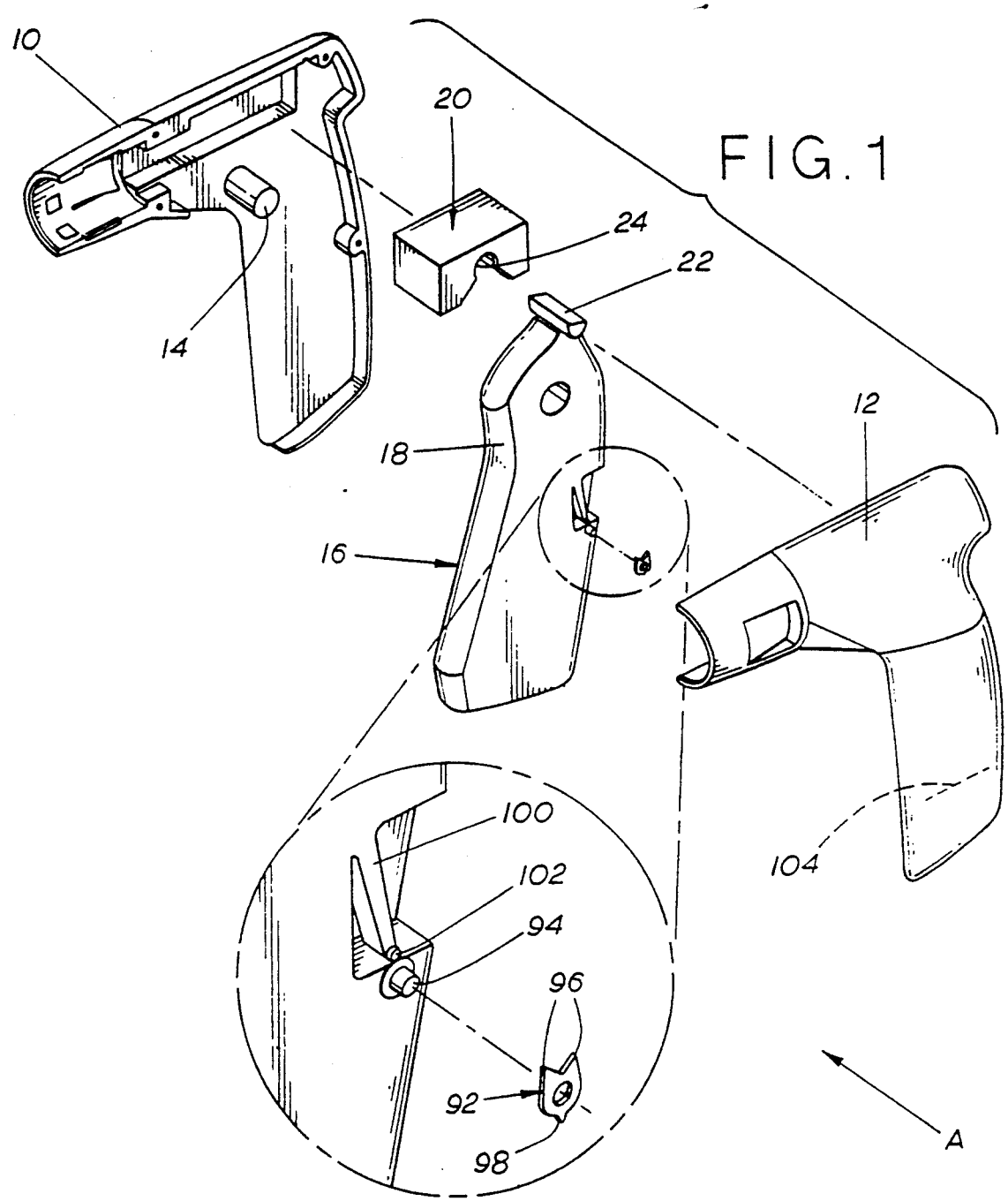

Some of the details of the operation of the apparatus A are illustrated in FIGS. 16-19 of U.S. Pat. No. 4,951,860. Briefly, to review, the apparatus A as shown in FIG. 1, there are handle portions 10 and 12 which are made to be pushed together to form the trigger housing of the apparatus A. Inside the housing portions 10 and 12 is a pivot pin 14 which extends through trigger 16. The leading edge 18 of trigger 16 extends beyond joined housing halves 10 and 12. It is depressed inwardly to actuate the apparatus A. Trigger 16 pivots on pin 14 when surface 18 is grabbed by the surgeon's hand and depressed inwardly. The pivot action results in displacement of drive block 20 which is connected to trigger 16 at tab 22. Tab 22 loosely fits inside a slot 24 in drive block 20. Depressing trigger 16 moves drive block 20 distally against form tool 26. Form tool 26 reciprocates over track cover panel 28. Track cover panel 28 has a slot 30 to accommodate the distal end of spring 32. The distal end of spring 32 bears on a stop (not shown) in upper barrel housing 34. Depressing the trigger 16 inwardly pushes drive block 20 distally against form tool 26, compressing spring 32. Release of the trigger 16 allows spring 32 to push the form tool 26 proximally against drive block 20 pushing trigger 16 outwardly.

Figure 12:
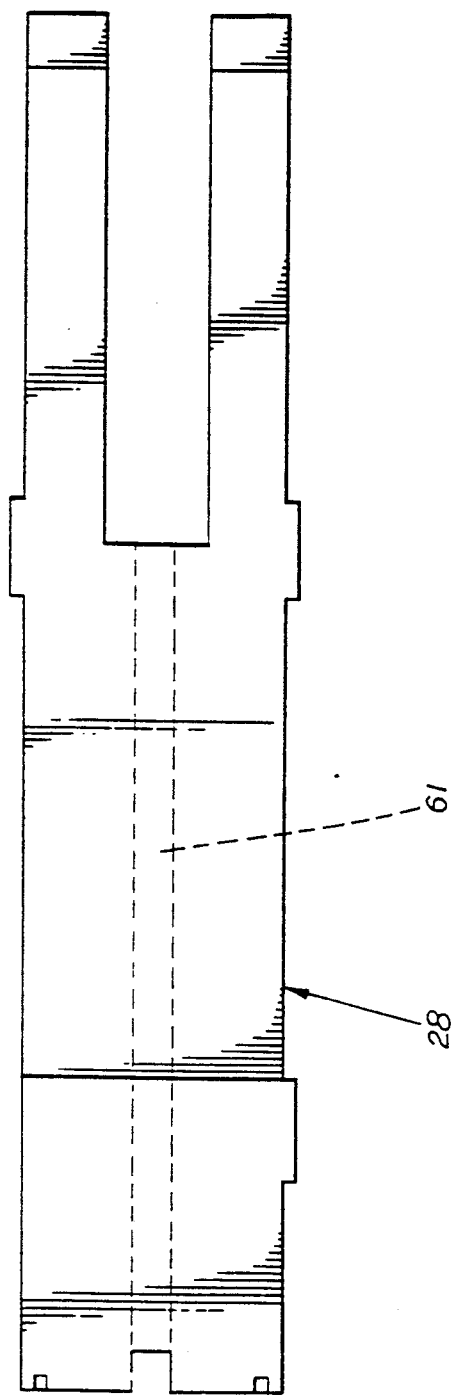
FIGS. 12 and 12(A-B) are front, side, and top views of the staple track cover.
Figure 12A:
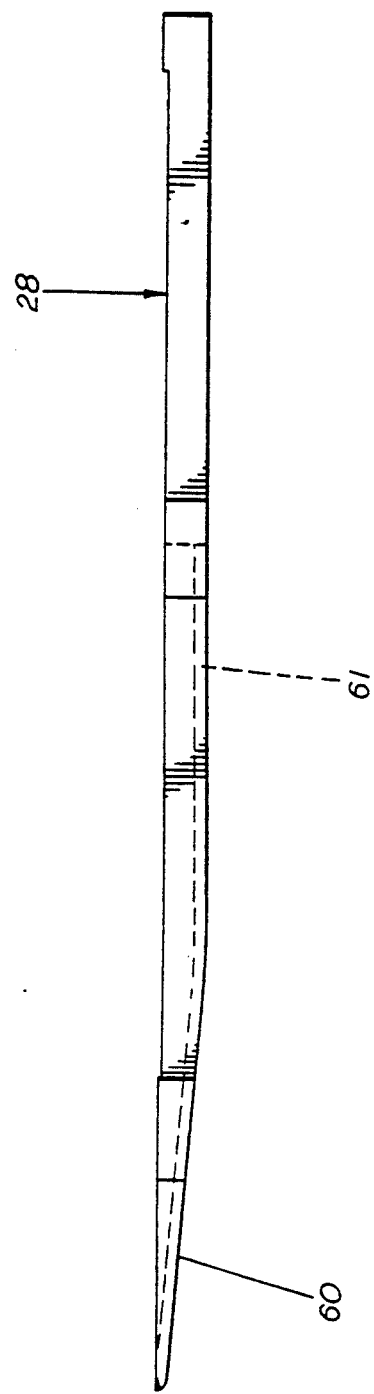
Figure 12B:
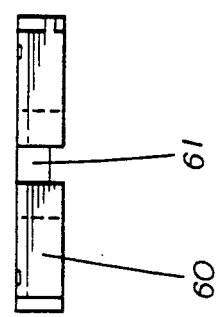

The housing 34 has a mating section 36 which is shown in detail in FIG. 3. Housing 36 includes a staple track 38. Staple track 38 accommodates staples 40 having the configuration shown in FIG. 1. The series of staples 40 housed in staple track 38 are pushed distally by staple pusher 42 shown in detail in FIG. 2. The staple pusher 42 is biased by a spring 44 which is mounted over a guide 46. Guide 46 has a pair of offset outwardly biased tabs 48 which are adapted to be engaged in groove 50 (see FIG. 3). It is within the scope of the invention to provide multiple grooves 50 offset from each other to accommodate a loading of different amounts of staples in the staple track 38. Additionally, the amount of pre-load on spring 44 can be adjusted by using a multiplicity of grooves 50 to provide initial compression to spring 44 depending on the number of staples loaded and in which particular groove 50 the tabs 48 are set to engage. After setting the staples in the staple track so that their legs 52 (see FIGS. 1, 3, and 4) extend into troughs 54 which extend from staple track 38, the cover 28 is installed into housing 36. Details of the cover are illustrated in FIG. 12.

Figure 2:
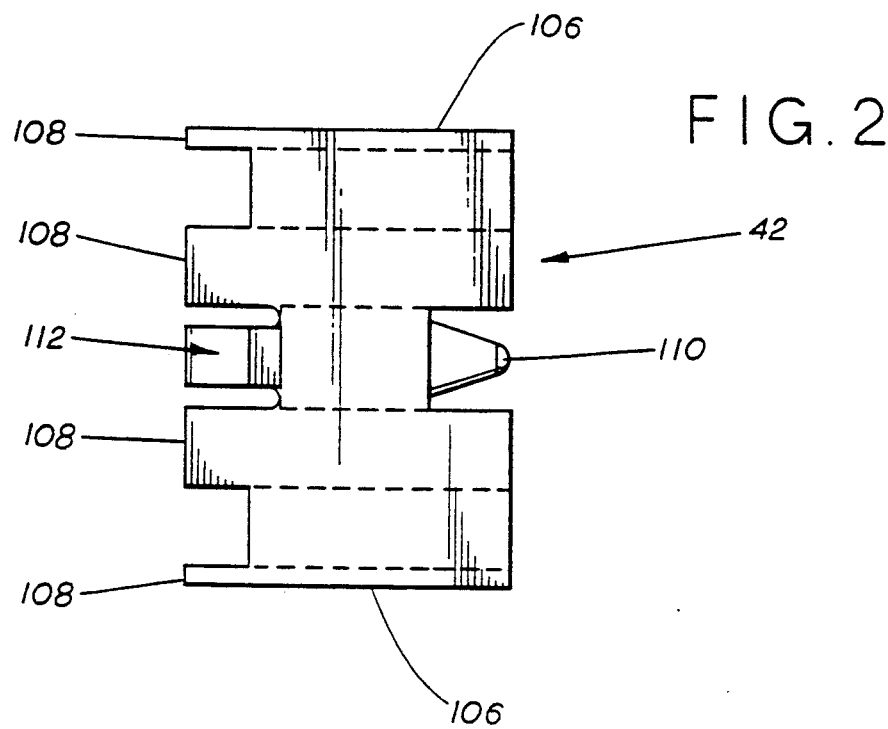
FIGS. 2 and 2(A-B) are front, side, and top views of the staple pusher.
Figure 2A:
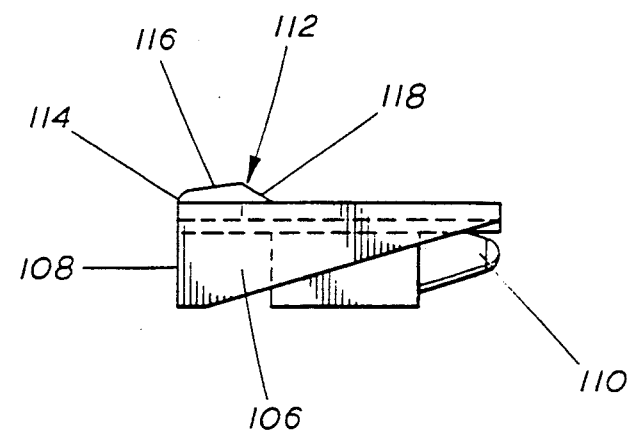
Figure 2B:
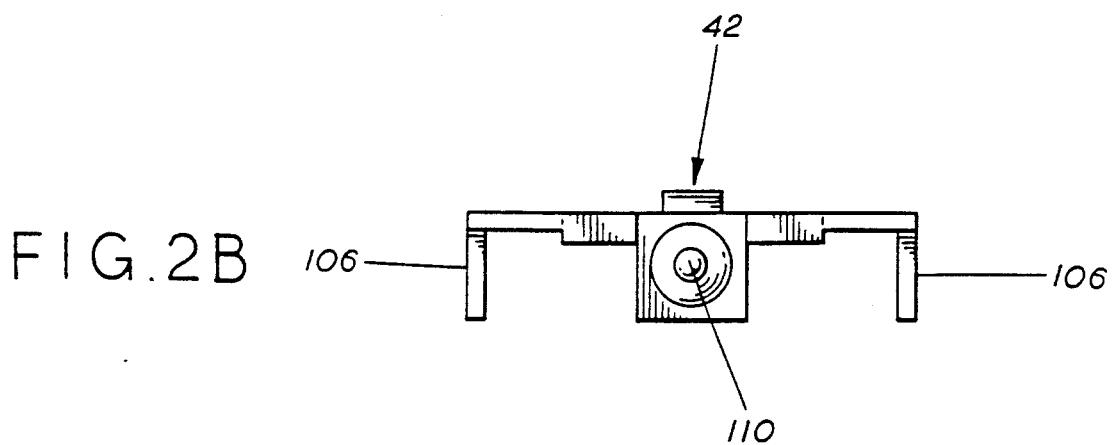

An important feature of the inclined portion 58 of the staple track 38 is that it accommodates the use of the "fin" or tab 112 on the top of the staple pusher 42 (see FIG. 2). In order to perform its function, fin 112 must bridge the distance between the staple track 58 and the form tool path 56 (see FIG. 8). Due to the incline in staple track 58, this distance is reduced at the point of feed. The fin 112 must travel in a clearance slot 61 (see FIG. 12) cut into the staple cover 28 which separates the staple track 58 and the form tool path 56. If the staple cover 28 were of a constant thickness, the required clearance slot would split the cover 28 in two, destroying its functionality. The variable thickness, i.e., the taper/incline of the cover panel 28 prevents this. The distal taper in the staple cover 28 allows structural strength in the proximal portion of the staple track cover 28. This rigidity bolsters the strength of section 36 and prevents staple binding due to warpage of the staple path in the track 38 if section 36 flexes. The thick proximal end allows the additional rigidity. The thinner distal end reduces the lift height of the staples while still allowing use of a groove to accommodate the fin or tab 112 which travels in the groove or slot 61. A split cover 28 can be used to accommodate tab 112 but the advantages of additional rigidity would not be present.

Another feature of the invention is illustrated by a detailed review of FIGS. 3 and 10. Looking at the elevation view in FIG. 3, it can be seen that the staple track 38 for its proximal portion is parallel to the staple form path 56 (see FIG. 3). Thereafter, there is an upward transition, preferably at about five degrees (5°) toward form path 56 for the distal portion of the staple track 38. This portion of staple track 38 that is upwardly inclined is identified by numeral 58. The upwardly sloping portion 58 of staple track 38 allows reduction of the profile of track cover panel 28 at its distal end as shown in FIG. 12. The cover 28 has a tapered portion 60 whose angle of taper generally conforms to the angle of staple track 38 at the inclined portion 58. It can then be seen in FIGS. 1 and 3 that the profile of the nose portion 62 is reduced due to the inclination of the staple track 58. Further reduction in the distal profile at nose 62 is accomplished by a taper 64 in housing 34 as shown in FIG. 1.

As previously stated, the form tool 26 is pushed distally by drive block 20. Form tool 26 has a lug 66 which extends upwardly into slot 68 of drag tool 70 (see FIG. 1). Slot 68 is longer than lug 66 to allow relative movement between form tool 26 and drag tool 70. Form tool 26 has a notch 72 between a pair of lands 74. The lands 74 bear against crossbar 76 of staple 40 and move the staple distally against anvil 78. Anvil 78 is fixedly mounted to housing member 34 and has an abutment surface 80 which is situated in alignment with notch 72 so that forward motion of the drag tool 26, pushing a staple 40 in form path 56, results in lands 74 bending the staple around abutment surface 80 which projects into the form path 56.

Drag tool 70 has a pair of fingers 82 disposed on drag tool 70 to drag in the path 56 so that upon proximal movement of form tool 26 after it has reached its full distal movement a gap exists in the plane of path 56 between fingers 82 and lands 74. The staple pusher 42 pushes the staples in track 58 forward in such a manner that as the form tool 26 moves proximally from its most distal position, the gap between fingers 82 and lands 74 positions itself above the crossbar of the next staple 76. The pushing action of staple pusher 42 moves the crossbar 76 of the next staple 40 into path 56 and into the gap between fingers 82 and lands 74. The staple 40 is then further drawn proximally awaiting a subsequent depression of trigger 16 to repeat the cycle. To ensure that a gap is in fact formed when form tool 26 moves in a proximal direction, the slot 68 is made larger than the lug 66 allowing fingers 82 to lag behind the proximally advancing form tool 26 so that the next staple 40 is trapped in the gap.

It should be noted that while spring 32 biases form tool 26 in the proximal direction, spring 84 bears against tab 86 on drag tool 70. Since the drag tool 70 is biased distally upon the proximal return of form tool 26, the existence of a gap is ensured as spring 84 pushes drag tool 70 distally relative to the proximal motion of form tool 26. As a result, a gap is formed between fingers 82 and lands 74 to allow the next staple 40 to be captured and moved proximally within path 56. When forming a staple and moving form tool 26 in the distal direction, the drag tool 70 contacts a stop at a certain point and, due to its thin construction at its distal end, allows fingers 82 to be pushed vertically out of the way of path 56 as the oncoming staple 40 moves toward anvil 78.

As the form tool 26 reaches its distal-most point having formed the staple 40 by bending it around abutment surface 80, the ejector spring 88, preferably having a pair of fingers 90, bears on the crossbar 76 of staple 40 and pushes it down and around abutment surface 80 to complete the staple ejection operation. It should be noted that the ejector spring 88 is not operative to eject the staple until the trigger 16 is depressed fully inwardly completing the distal range of motion of form tool 26.

Referring also to the detailed view, which is a portion of FIG. 1, the ratchet mechanism, whose function it is to require the trigger 16 to be fully depressed before it can be let out and vice-a-versa, to be completely released before it can be depressed again, is illustrated in detail. The function of this mechanism is similar to that shown in FIGS. 3 and 4 of U.S. Pat. No. 4,662,555. What is employed is a pawl 92 which can pivot on pin 94. Pawl 92 has a pair of ears 96 and an engagement point 98. Finger spring 100 has a tab 102 that rides between ears 96. Located within handle portion 12 is a bearing surface 104 on which point 98 can ride. As the handle 16 is being depressed to move the drive block 20 distally, such motion is permissible since point 98 is offset and dragging to the rear with respect to trigger 16. However, if the trigger 16 is released before its completed stroke, the point 98 digs into surface 104 and prevents outward movement of trigger 16. Ultimately, when the trigger 16 is fully depressed, the pawl 92 runs off beyond the edge of surface 104 causing rotation of pawl 92 on pin 94. Thereafter, as the spring 32 pushes the form tool 26 against the driveblock 20 in a proximal direction, point 98 is once again dragging allowing the trigger 16 to come all of the way out from the handle portions 10 and 12. Similarly, when the trigger 16 is all of the way out, the pawl 92 runs off the end of surface 104 and rotates about pin 94 to permit redepression of trigger 16.

The unique features of the staple pusher illustrated in FIGS. 2 and 4–8 will now be described. The staple pusher 42 is shown in FIG. 2. It has a pair of outriggers 106 that ride in grooves 54 (see FIG. 3). The leading edge 108 of each of the outriggers 106 bears against the legs 52 of the rearmost staple 40 in the staple track 38. Spring 44 bears on point 110. At the distal end of pusher 42 is the tab 112. Tab 112 has a rounded distal edge 114 leading to a top 116 followed by a downwardly inclined surface 118.

Figure 4:
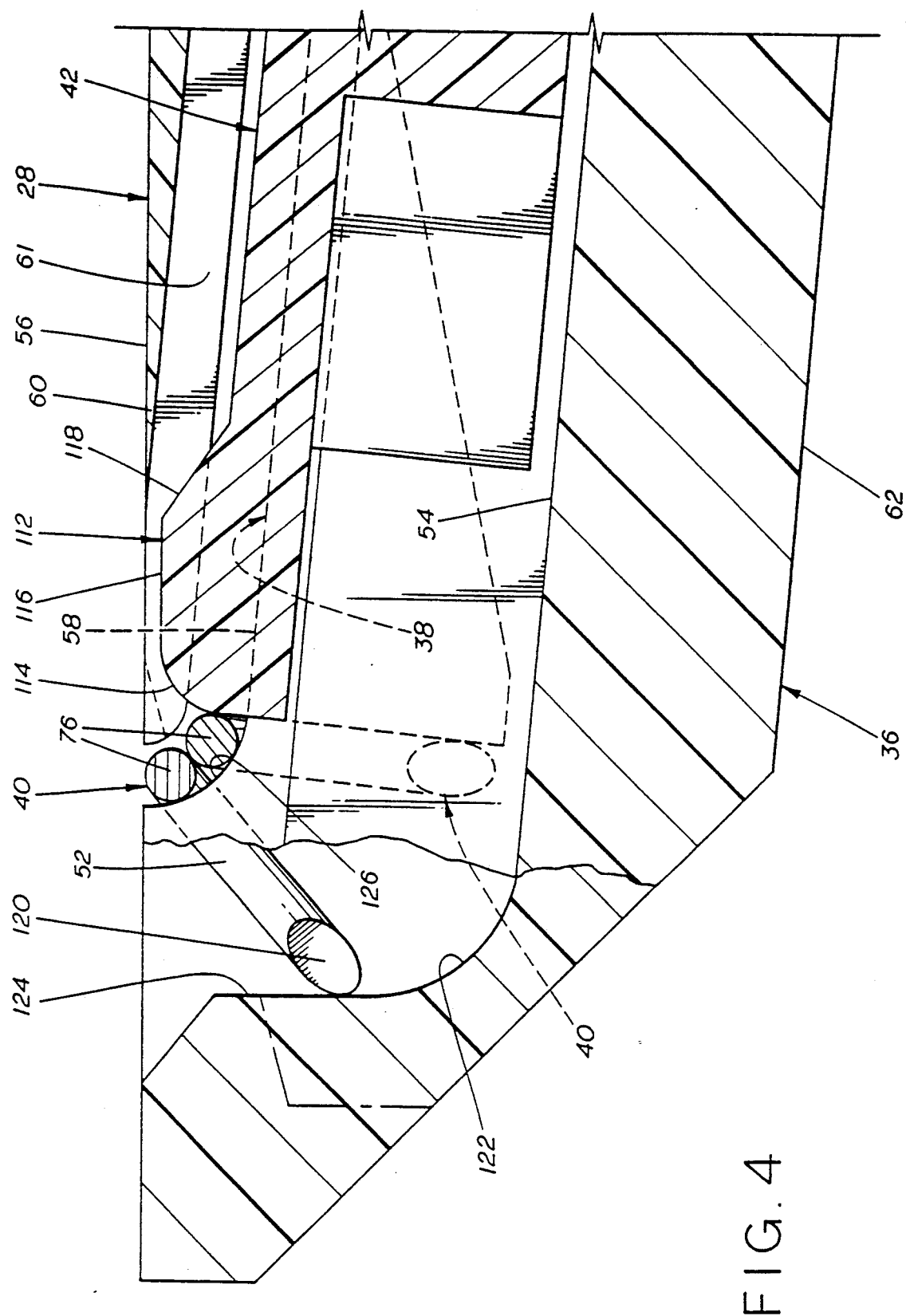
FIGS. 4 through 8 is a side elevational view of the staple pusher showing sequentially how the last two staples in the staple track are fed into the staple path for formation.
Figure 5:
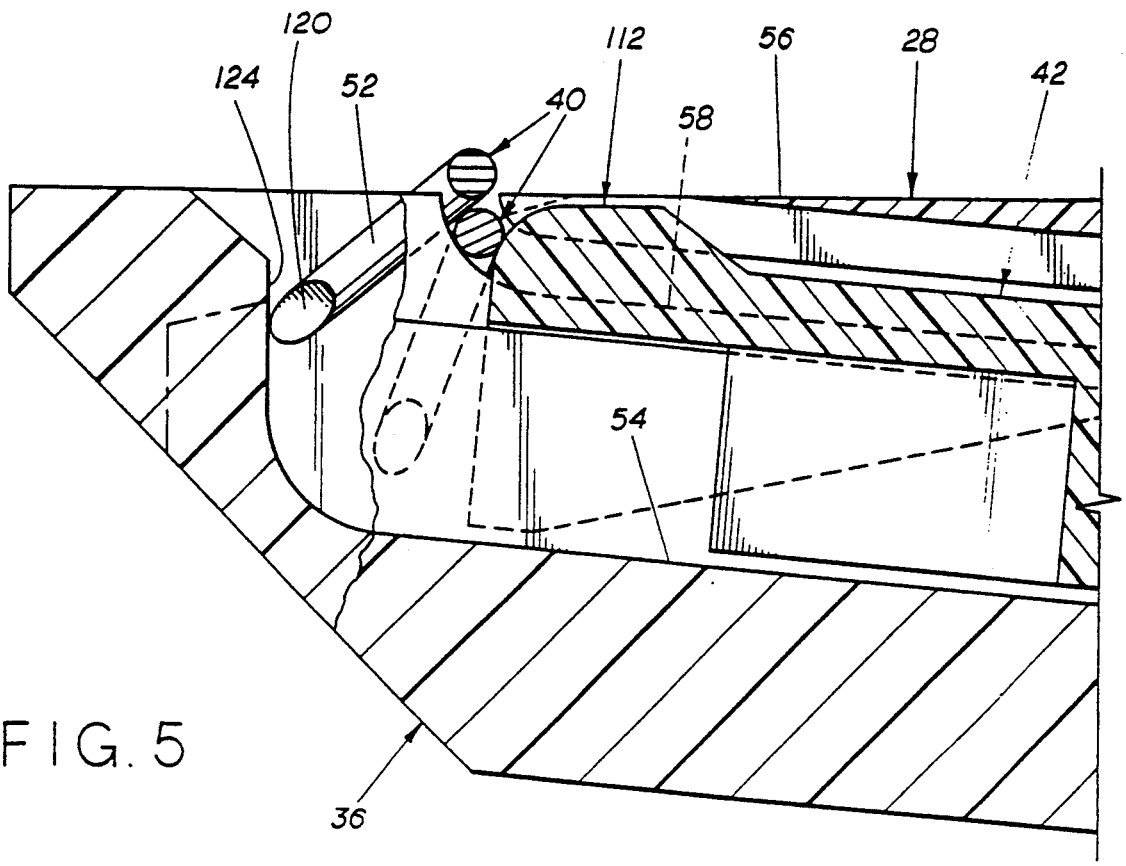

The operation of these components is as seen in FIGS. 4–8. In FIG. 4, the last two staples remain in the inclined portion 58 of the staple track 38. Each of the staple legs 52 has a bottom bevel 120. The housing 36 is formed having a curve 122 leading to a wall 124. As the pusher 42 advances the second to the last staple (shown in FIG. 4), it starts to push it up curved surface 126. At that point, the staple pusher 42 is still riding in the inclined portion 58 of staple track 38. Further distal movement of pusher 42 (as shown in FIG. 5) displaces the second to the last staple 40 upwardly into the form path 56. There, as previously described, when the form tool 26 makes its proximal return trip, the gap between fingers 82 and lands 74 appears and then the second to the last staple moves up and is drawn back along path 56. The beveled ends 120 ride along wall 124 as an aid to the controlled rotation of the staple 40 fully into path 56 as form tool 26 concludes its proximal travel. The use of wall 124 to guide the staple 40 is to be compared to that illustrated in FIGS. 17–19 of U.S. Pat. No. 4,950,186. There, the staples do not bear on the wall but are engaged by an overhanging ledge and retain in that position until the gap between fingers 82 and lands 74 engages crossbar 76 of the staple and pulls the staple out from under the ledge and fully into the form path 56. Such a detail could be employed in the invention as an alternative way to guide the legs 52 of the staple 40 as it is pulled into path 56.

Figure 6:
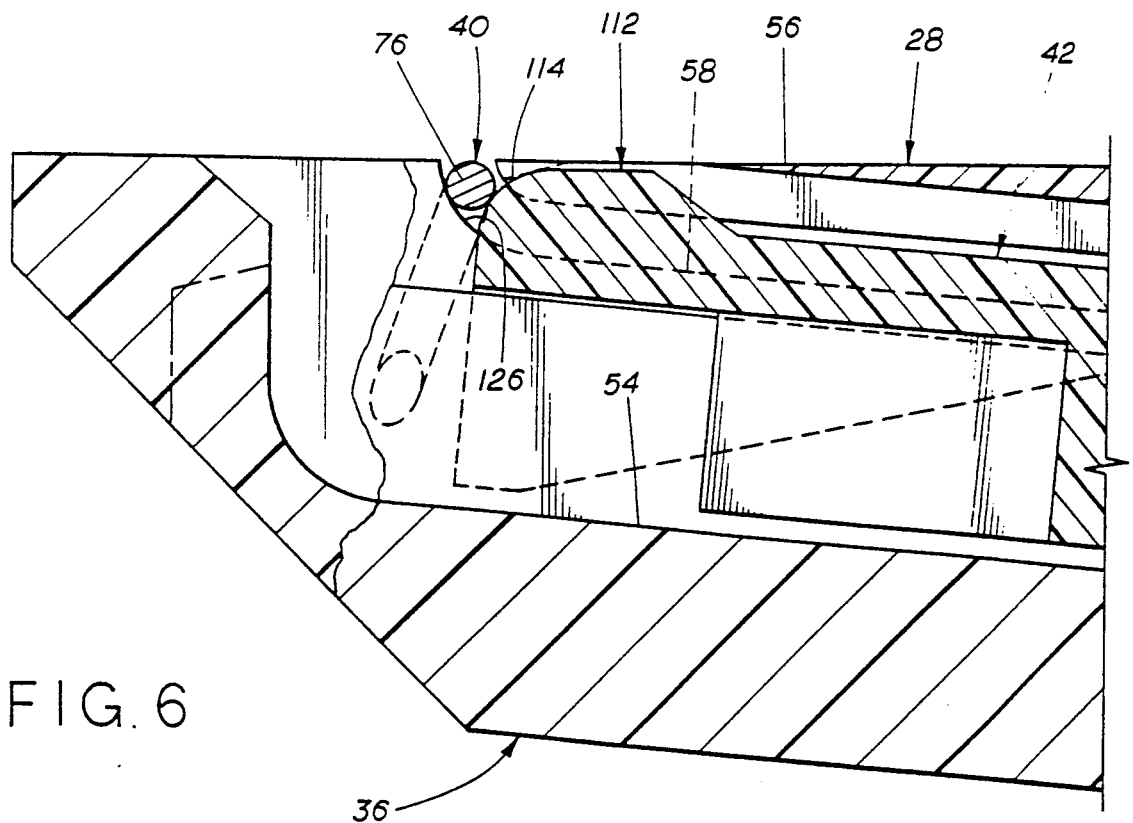
Figure 7:
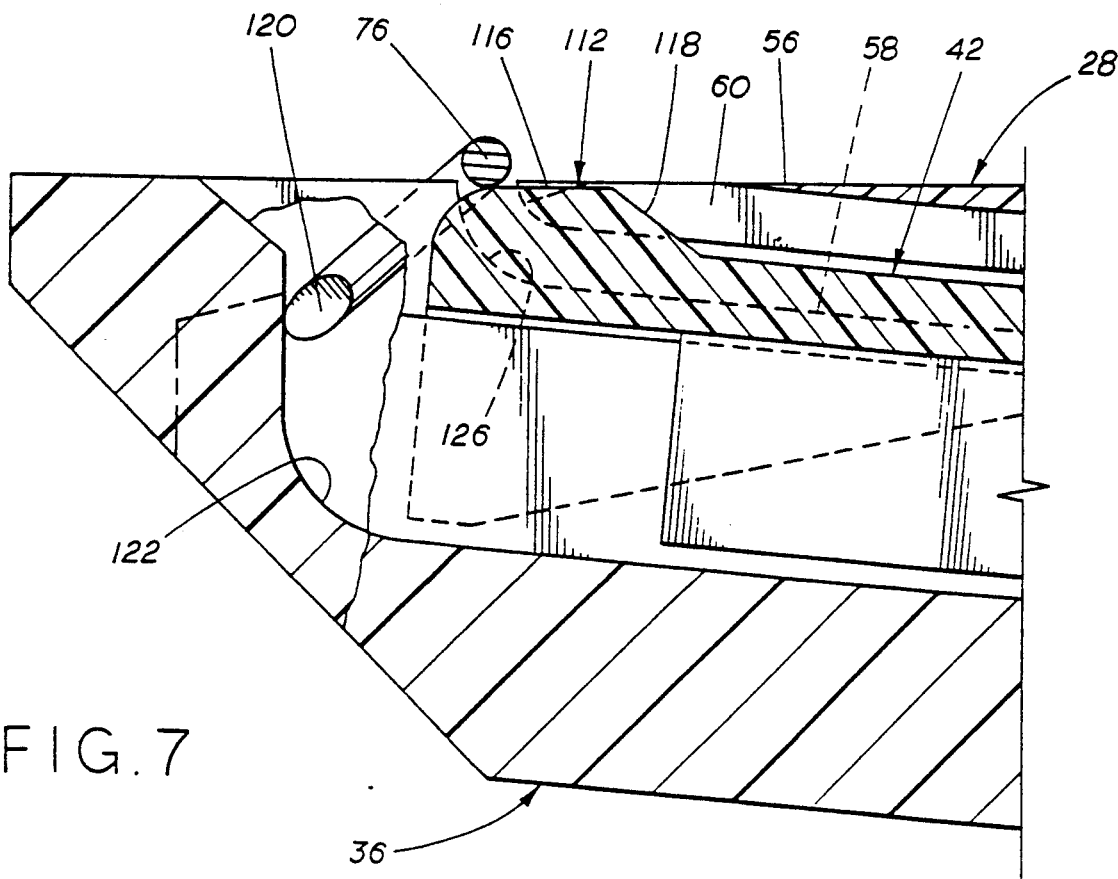
Figure 8:
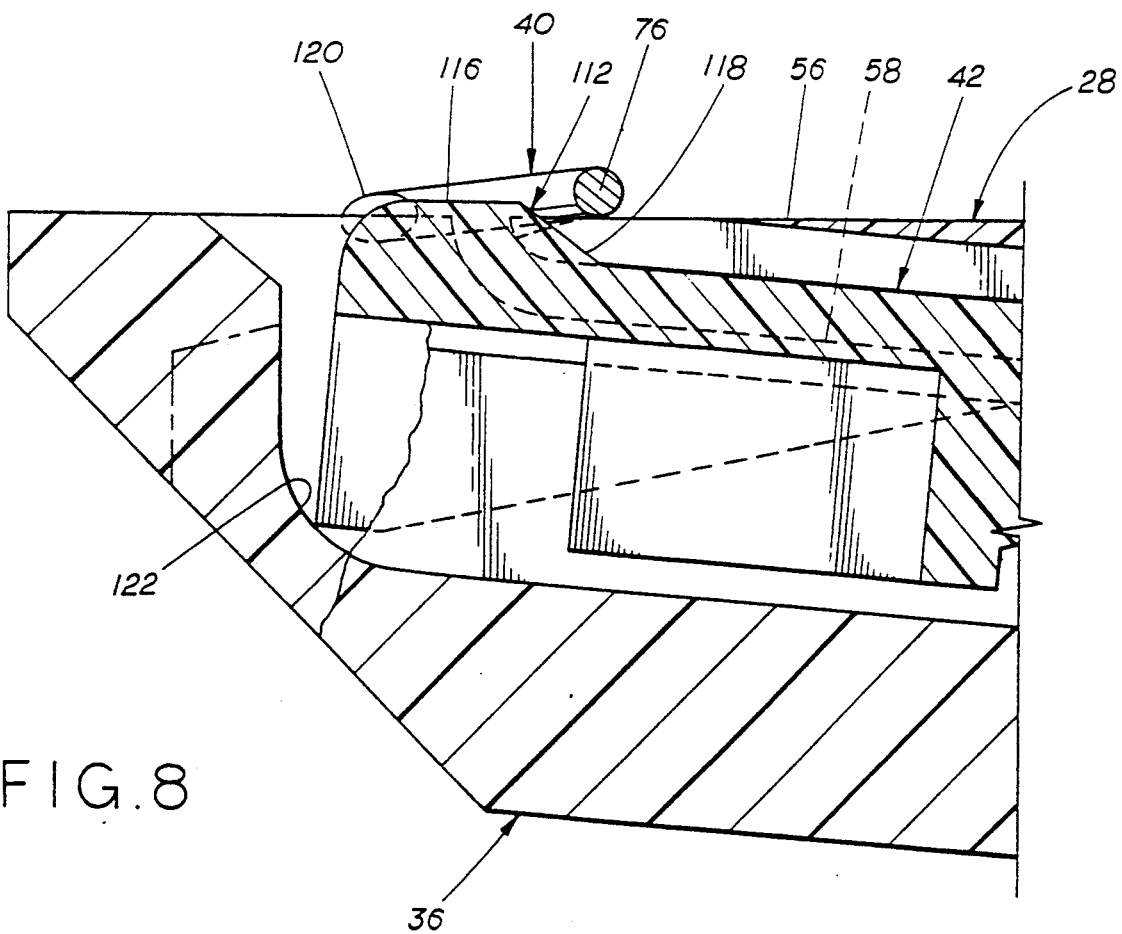

FIG. 6 shows only one remaining staple which has a crossbar 76 in contact with curved surface 114. FIGS. 6 and 7 show the while the inclined path 58 transitions to curved surface 126 from the point of view of support of crossbars 76, the staple pusher continues to translate linearly along the plane of staple track 58. This continuing linear translation with respect to the angled path 58 results in pushing crossbar 76 up along curved surface 114. As form tool 26 moves proximally, the gap "appears," allowing upward movement into the form path 56 where the staple crossbar 76 can be grabbed by the fingers 82 of drag tool as it moves proximally. After it moves upward into the gap, the staple is temporarily held there by surface 116. Once the crossbar 76 is caught by the fingers 82 in the gap they make with lands 74, the staple is pulled fully into path 56 as shown in FIG. 8. Ultimately, when the form tool 26 completes its travel proximally, the crossbar 76 down to beveled end 120 of the last staple 40 is fully within form path 56. As shown in FIG. 8, when the form tool is ready to advance distally to form the last staple 40, tab 112 still projects into the form path 56. Accordingly, the ramp surface 118 is provided so that the advancing staple 40 has its crossbar 76 hit inclined surface 118. The staple pusher 42, once it is in the position shown in FIG. 8, is designed so that tab 112 can be displaced downwardly, thereby allowing the last staple 40 to advance to the end of form path 56. This bending action gets tab 112 out of the way of form path 56.

Figure 11:
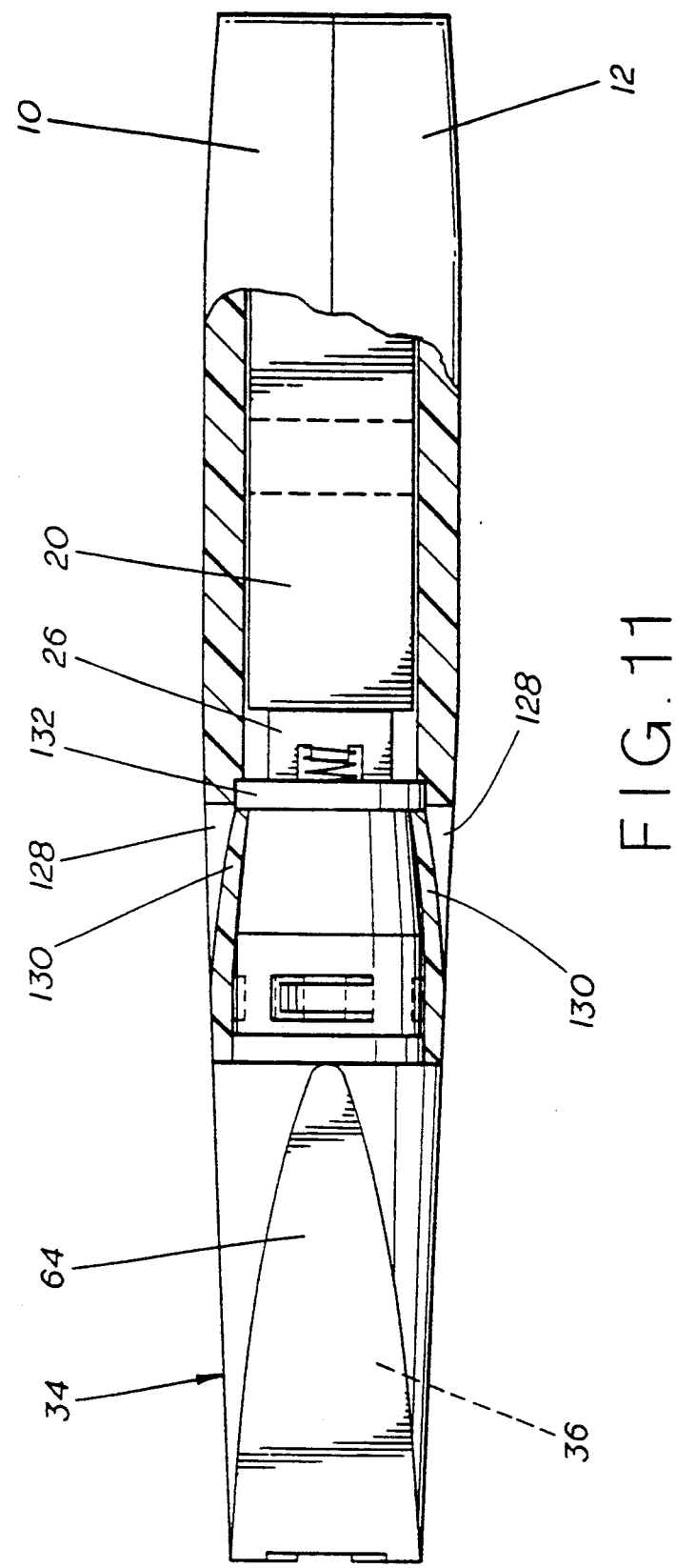

FIGS. 9-11 indicate a snap fit between the trigger assembly composed of halves 10 and 12 and the nose assembly which is held within members 36 and 64. The trigger assembly has a groove 128 formed behind fingers 130 which are biased inwardly. Housing members 36 and 64 have a proximal flange 132. As the nose portion (housing 64 and 36) is inserted into the handle portion 10 and 12, flange 132 displaces fingers 130 outwardly as shown in FIG. 10. Further insertion of the assembly into the trigger housing allows the fingers 130 to snap back and engage flange 132. At that point, the nose is secured to the trigger housing 10 and 12 and cannot be removed. The modular design has several advantages. It reduces manufacturing costs and inventory since individual modules can be used in subsequent product designs. The use of the modular design also saves costs and molding parts since there are no undercuts or cores required. Further, the geometry of the design makes it a positive feedback system. Greater applied force leads to increased retention effectiveness. The design also provides good strength with little deflection and offers the security that the nose, once it is snapped into place, cannot be removed by the user.

The assembly of the nose to the trigger housing 10 and 12 can also be accomplished in a manner that allows subsequent release. The nose assembly can be formed having a plurality of collet fingers, the edges of which form a flange. The collet fingers can then be inserted into the trigger housing to engage slots in the trigger housing 10 and 12. Once the collet members in the nose expand radially into the openings in the trigger housing, the engagement is complete. Detachment then follows by depressing the flanges at the edges of the collet fingers on the nose sufficiently inwardly so that the nose can be pulled out of the trigger housing 10 and 12.

The positive displacement feature of the connection between the trigger 16 and the drive block 20 is an improvement over the gear tooth assembly used in U.S. Pat. No. 4,951,860. Some flexibility of movement is provided between tab 22 and slot 24 to prevent the drive block 20 from binding as trigger 16 pivots about pin 14. This design is capable of transmitting considerable force and is simple to assemble, and can be made of parts which are simple to produce and provide excellent "feel" and leverage.

Referring to FIG. 12, the importance of the thin distal end of the cover 28 is illustrated. As shown in FIGS. 5 and 7, the staple pusher 42 must push the staple 40 above the cover 28 and into path 56. Thus, the use of a thinner distal end 60 of the cover 28 reduces the height which the staples must be raised to get them into path 56. It is the upward slope 58 of the staple path 38 that allows the use of a thin distal end 60 of the staple cover 28.

It should be noted that the reliefs created by the use of outriggers 106 on staple pusher 42 (see FIG. 2) allow staple pusher 42 to move along the inclined portion 58 beyond the point which it would normally have hit up against curved surface 122 or wall 124. This additional motion allows lifting of last staples.

The foregoing disclosure and description of the invention are illustrative and explanatory thereof, and various changes in the size, shape and materials, as well as in the details of the illustrated construction, may be made without departing from the spirit of the invention.

What is claimed is:

1. A surgical stapler, comprising:
a housing;
means for storing staples in said housing;
means, at least in part, in said housing for forming staples, said means further comprising a forming path;
said storing means further comprising a staple track;
said forming path communicating with said storing means;
a staple pusher operable along said staple track;
biasing means to selectively move said pusher along said track;
said biasing means having a proximal and distal end;
mounting means in said housing for selectively fixedly mounting at least one end of said biasing means to said housing in a plurality of locations;
said biasing means acting on said pusher, to selectively apply a variable preload force, resulting from the location of said mounting means that is selected, through said staple pusher to a variety of staple counts loaded into said staple track.

2. The apparatus of claim 1, wherein:
said pusher operable in said staple track from a proximal position where the track is loaded with staples toward a distal position where the staples have been displaced from said staple track;
means for camming the last remaining staples in said staple track as said pusher approaches said distal position to impart an upward component of movement to those staples resulting from said pusher moving in a different direction than said staples.

3. A surgical stapler, comprising:
a housing;
means for storing staples in said housing;
means in said housing for forming staples, at least in part, said means further comprising a forming path;
said storing means further comprising a staple track;
said forming path communicating with said storing means;
a staple pusher operable along said staple track;
biasing means to selectively move said pusher along said track and into said forming path;
said biasing means having a proximal and distal end;
mounting means in said housing for selectively fixedly mounting at least one end of said biasing means to said housing in a plurality of locations;
said biasing means acting on said pusher, to selectively apply a variable preload force, resulting from the location of said mounting means that is selected, through said staple pusher to a variety of staple counts loaded into said staple track;
said staple forming means displacing said staple pusher out of said forming path as it approaches said distal position, toward said staple to be formed, thus imparting a force on said staple pusher.

4. A surgical stapler, comprising:

a housing;

means for storing staples in said housing, including a penultimate staple;

means in said housing for forming staples, said means further comprising a forming path;

said storing means further comprising a staple track;

said forming path communicating with said storing means;

a staple pusher operable along said staple track;

biasing means to selectively move said pusher along said track and into said forming path;

said biasing means having a proximal and distal end;

mounting means in said housing for selectively fixedly mounting at least one end of said biasing means to said housing in a plurality of locations;

said biasing means acting on said pusher, to selectively apply a variable preload force, resulting from the location of said mounting means that is selected, through said staple pusher to a variety of staple counts loaded into said staple track;

said staple pusher having at least one camming surface thereon, said staple-forming means engaging said camming surface to cam the staple pusher out of the forming path as said staple-forming means advances distally to form the penultimate staple in said track.

* * * * *